US005672762A

United States Patent [19]

Vedage et al.

[11] Patent Number: 5,672,762
[45] Date of Patent: Sep. 30, 1997

[54] HYDROGENATION OF NITRILES TO TERTIARY AMINES

[75] Inventors: Gamini Ananda Vedage, Bethlehem; John Nelson Armor, Orefield, both of Pa.

[73] Assignee: Air Products and Chemicals, Inc., Allentown, Pa.

[21] Appl. No.: 631,280

[22] Filed: Apr. 12, 1996

[51] Int. Cl.[6] .................................................. C07C 209/48
[52] U.S. Cl. .................................................. 564/490
[58] Field of Search ..................... 564/490, 448, 564/491, 492, 493

[56] References Cited

U.S. PATENT DOCUMENTS 3,152,185 10/1964 Zvejnieks ........................... 260/583
3,177,258 4/1965 Rylander et al. ................... 260/611
3,673,251 6/1972 Frampton et al. .................. 260/563
4,297,512 10/1981 Mainusch et al. .................. 564/490

FOREIGN PATENT DOCUMENTS 182166 4/1977 U.S.S.R. ......................... C07C 85/12

OTHER PUBLICATIONS

*Studies in Surface Science and Catalysis*, Vol. 27 (1986), Chapter 4, "Hydrogenation of Nitriles," by Jiri Volf and Josef Pasek.

*Primary Examiner*—Brian M. Burn
*Attorney, Agent, or Firm*—Mary E. Bongiorno

[57] ABSTRACT

Improved selectivity to tertiary amine production is obtained by the addition of an aliphatic or aromatic halide to the feed during the catalytic hydrogenation of saturated or unsaturated aliphatic or cycloaliphatic nitriles.

20 Claims, No Drawings

HYDROGENATION OF NITRILES TO TERTIARY AMINES

TECHNICAL FIELD OF THE INVENTION

The hydrogenation of saturated or unsaturated aliphatic and cycloaliphatic nitriles to produce tertiary amines.

BACKGROUND OF INVENTION

Catalytic hydrogenation of nitriles to form primary, secondary and tertiary amines is known. An overview of this technology can be found in *Studies in Surface Science and Catalysis*, Vol. 27 (1986), Chapter 4, "Hydrogenation of Nitriles," by Jiri Volf and Josef Pasek. Selection of catalysts is important in obtaining selectivity in the product. For example, platinum group metals are known to be effective in the hydrogenation of nitriles to form secondary and tertiary amines. Platinum and palladium catalysts have been shown to be particularly effective at yielding high amounts of tertiary amines. Among the problems associated with selective formation of tertiary amines vs primary or secondary amines from nitriles is the loss of product selectivity with catalyst use. When selectivity to tertiary amine formation drops below about 90%, catalyst lots must be replaced and used catalysts must be washed before re-use, even if the catalyst is still active. The drop in selectivity can occur after only one catalyst use. In practice, the hydrogenation process is often carried out in the presence of a solvent in order to enhance conversion to amines and to minimize catalyst poisoning. In the case of solid nitriles, solvents ease handling of the nitriles and are useful for continuous hydrogenation.

Below are described representative patents which illustrate the preparation of tertiary amines from nitriles:

U.S. Pat. No. 3,177,258 (Rylander, et al.) discloses use of ruthenium combined with platinum, palladium or rhodium as catalysts for hydrogenating organic compounds such as aliphatic nitriles, aromatic nitriles, and hydroxylamines. Hydrogenation of propionitrile using ruthenium and platinum or ruthenium and palladium gave conversion products which were entirely tertiary amines.

U.S. Pat. No. 3,673,251 (Frampton, et al.) discloses a cyclic process for preparing secondary or tertiary mono-, di-, or polyamines by catalytic reductive amination of mono-, di- or polynitriles in the presence of a hydrogenation catalyst such as Raney nickel, Raney cobalt, platinum, and the like. Continuous removal of ammonia is necessary to drive the reaction to the formation of secondary and tertiary amines.

U.S. Pat. No. 4,297,512 (Mainusch, et al.) discloses a process for preparation of triethylamine by gas phase hydrogenation of acetonitrile using a Group VIII catalyst on a lithium aluminum spinel support. The process can be carried out in the presence of up to 5% by weight of monoethylamine and/or diethylamine.

SU-182,166 (Vvedenskii) discloses production of tertiary amines by hydrogenation of 7–9 carbon nitriles over a nickel on kieselguhr catalyst at elevated temperature and pressure. The yield of amines is 50–55%; secondary and primary amines are recirculated.

SUMMARY OF THE INVENTION

This invention relates to an improvement in a process for the production of tertiary amines by catalytic hydrogenation of saturated or unsaturated aliphatic or cycloaliphatic nitriles, preferably having 2 to about 15 carbons. The improvement is directed to the addition of a small amount of an organic halide to the catalyst system which results in enhanced selectivity to tertiary amine formation.

DETAILED DESCRIPTION OF THE INVENTION

Catalytic processes for the hydrogenation of aliphatic or cycloaliphatic nitriles are well known in the art, and are exemplified in the patents discussed in the background of the invention. The process can be carried out in batch or continuous mode.

Nitriles used in the hydrogenation process include saturated or unsaturated aliphatic mono and dinitriles, preferably up to 15 carbons, and most preferably having up to 10 carbons. For example, acetonitrile, acrylonitrile, methacrylonitrile, propionitrile, isopropionitrile, butyronitrile, valeronitrile, capronitrile, cyclohexylnitrile, cyclopentylnitrile, cyclohexenedinitrile, cyclopentenedinitrile, and dodecanenitrile.

Appropriate hydrogenation catalysts are those used in the prior art, for example Group VIII metals such as platinum, palladium, rhodium, ruthenium, nickel, and cobalt, and copper, or mixtures thereof. The catalyst is preferably carried on a support such as alumina, silica, titania, magnesium oxide or carbon or mixtures thereof. For reasons of efficiency and economy, the preferred catalyst is palladium and the preferred support is alumina.

The amount of metal catalyst on the support can vary from about 0.5% to about 10%; typically about 5%. The level of catalyst used for effecting hydrogenation of a nitrile are the same as those commonly used in conventional hydrogenation processes of this type and is typically based on the weight of nitrile. Broadly, the metal loading will vary between about 0.1% and about 10% by weight, preferably about 1% to 5% by weight, based on the weight of nitrile.

An organic halide is added to the catalyst to maintain and/or enhance the selectivity toward production of tertiary amines. The organic halide has the formula $RX_n$ in which R is an aliphatic or aromatic group having 1–10 carbon atoms, preferably 2–5 carbons, X is chloride, bromide or iodide, and n is 1 to the total number of replaceable hydrogens in R. Examples of appropriate organic halides for use in this invention are: dichloroethane, carbon tetrachloride, hexachloroethane, monochloroethane, monobromoethane, and benzyl chloride. An aliphatic dihalide such as dichloroethane is preferred. It is well known that additives tend to deactivate catalysts; therefore the amount of organic halide is adjusted to limit deactivation and yet retain selectivity. The level of organic halide will vary from about 0.01% to about 5.0% by weight, preferably about 0.1 to 2.0% by weight, based on the weight of nitrile.

Although not intending to be bound by theory, it is believed that the organic halide acts as a catalyst promoter in shifting the reaction from production of primary or secondary amines to tertiary amines.

Effective conditions for catalytic hydrogenation of nitriles to tertiary amines are those conventionally used in the art. For example, hydrogenation temperatures can range from about 60° C. to 200° C.; preferably, 100° C. to 150° C. Hydrogenation pressure ranges from about 50 to about 1500 psi; preferably between 250 and 1000 psi. The hydrogenation can be carried out neat, however a conventional organic solvent such as benzene, tetrahydrofuran, or an alcohol is preferred. Polar solvents such as isopropanol are especially preferred.

EXAMPLES

The following examples are provided to illustrate various embodiments of the invention and are not intended to restrict the scope thereof.

In all of the examples, a batch process is used to hydrogenate butyronitrile in the presence of a commercial 5% palladium on alumina catalyst. From 0.1 to 2 wt. % of dichloroethane is added at the first or the fourth catalyst use in Examples 1 and 3 through 6. Example 7 is a comparative example showing the effect of an inorganic halide, lithium chloride, in place of dichloroethane in the catalytic hydrogenation of butyronitrile in isopropanol solvent. The following data were collected for each example: time for hydrogenation, % conversion of nitrile, and selectivity of product to primary, secondary, or tertiary amine.

Example 1

Dichloroethane (0.5 wt. %) added at 4th Catalyst Use (No Solvent)

A 300 ml batch reactor was used to carry out the hydrogenation at 500 psi and 1500 rpm stirring rates to minimize hydrogen mass transfer as a limitation to reaction rates. A catalyst charge of 1.5 g of 5% palladium on alumina was added to the pressure vessel followed by 100 g of butyronitrile. The reactor was pressurized with hydrogen to 450 psi and heated to 125° C. with agitation. Reactor pressure was then adjusted to 500 psi. The reactor was connected through a pressure controller to a ballast tank filled with hydrogen. The volume and hydrogen pressure of the ballast tank was chosen to be sufficient to provide the hydrogen necessary for the reaction without dropping the total pressure below 500 psi. The system volume was small enough so that the ballast pressure drop was an accurate measure of hydrogen consumed. Ballast pressure was followed versus time as a measure of the hydrogenation taking place. By calculating, the ballast pressure change (known volume), the molar hydrogen consumption was determined. When the reaction test was completed, the ballast line was closed, the reactor sealed, and the reactor purged with nitrogen. Product was removed through an internal filter. The catalyst was used four times and 0.5 wt. % dichloroethane (based on the weight of nitrile) was added to the feed at the fourth catalyst use. Selectivity to tertiary amine increased significantly from 86% in the third use to 96% at the fourth use; however the nitrile conversion decreased to 70%.

Example 2

No Dichloroethane added (Isopropanol Solvent)

The procedure of Example 1 was followed except that the feed was 100 g of 50% butyronitrile in isopropanol, the catalyst charge of 0.75 g of 5% palladium on alumina was used two times, and no dichloroethane was added. The rate of conversion was maintained through two catalyst uses, but selectivity to tertiary amine was less than 80% in both uses.

Example 3

Dichloroethane (2.0 wt. %.) added in 4th Catal st Use (Isopropanol Solvent)

The procedure of Example 2 was followed except that the catalyst charge was used four times and 2.0 wt. % (based on weight of nitrile) dichloroethane was added at the 4th catalyst use. The rate of conversion was maintained from the third to fourth uses and the addition of dichloroethane resulted in a jump in selectivity to tertiary amine from 57% in the third to over 90% in the fourth use.

Example 4

Dichloroethane (0.25 wt. %) added in 4th Catalyst Use (Tetrahydrofuran Solvent)

The procedure of Example 3 was followed except that 0.25 wt. % (based on weight of nitrile) dichloroethane was added at the 4th catalyst use and tetrahydrofuran was used as a solvent. As with isopropanol solvent, a drop in selectivity to tertiary amines is observed with successive catalyst uses. Addition of dichloroethane at the fourth catalyst use results in a dramatic increase in tertiary amine production to nearly 100%.

Example 5

Dichloroethane (0.1 wt. %) added in 1st Catalyst Use (Isopropanol Solvent)

The procedure of Example 2 was followed except that 0.1 wt. % dichloroethane (based on weight of nitrile) was added at the first catalyst use. No additional dichloroethane was added at the second use, although residual dichlorethane remains on the catalyst after the first use. Selectivity to tertiary amine decreased from about 95% in the first use to about 78% in the second use.

Example 6

Dichloroethane (0.5 wt. %) added in 1 st Catalyst Use (Isopropanol Solvent)

The procedure of Example 2 was followed except that 0.5 wt. % dichloroethane (based on weight of nitrile) was added at the first catalyst use. No additional dichloroethane was added at the second use, although residual dichlorethane remains on the catalyst after the first use. The second run was allowed to go overnight (835 minutes) before the product slate was analyzed; however, based on measurement of hydrogen uptake during the run, 75% conversion was obtained in 350 minutes; 90% conversion in 550 minutes; and 95% conversion in 800 minutes.

Example 7

Addition of 0.5 wt. % Lithium Chloride (Isopropanol Solvent)

The procedure of Example 2 was followed except that 0.5wt. % lithium chloride (based on weight of nitrile) was added instead of dichloroethane, and the catalyst was used once. Only 48.6% conversion to tertiary amine was observed.

RESULTS

The results of Examples 1–7 are set forth in Table 1 below.

TABLE 1

HYDROGENATION OF BUTYRONITRILE AT 125° C. AND 500 PSI PRESSURE USING 5% Pd/Al$_2$O$_3$[a] CATALYST (1.5 WT. % CATALYST LOADING)

| Example | Use | Solvent[b] | Additive[c] (wt. %) | Time (Min) | Conversion (%) | Selectivity Bu$_3$N (%) | Bu$_2$NH (%) | BuNH$_2$ (%) |
|---|---|---|---|---|---|---|---|---|
| 1 | 1 | None | None | 90 | 87 | 94 | 6 | 0 |
| (100 g feed) | 2 | None | None | 280 | 86 | 89 | 11 | 0 |
|  | 3 | None | None | 460 | 84 | 86 | 14 | 0 |
|  | 4 | None | EDCl (0.5) | 460 | 70 | 96 | 4 | 0 |
| 2 | 1 | IPOH | None | 90 | 99.5 | 79.5 | 20.4 | 0.1 |
| (100 g of 50% feed) | 2 | IPOH | None | 170 | 98 | 75.5 | 24.3 | 0.2 |
| 3 | 1 | IPOH | None | 80 | 97 | 80 | 12 | 0 |
| (100 g of | 2 | IPOH | None | 205 | 96 | 73 | 27 | 0 |
| 50% feed) | 3 | IPOH | None | 360 | 95 | 57 | 43 | 0 |
|  | 4 | IPOH | EDCl (2.0) | 350 | 95 | 91 | 9 | 0 |
| 4 | 1 | THF | None | 80 | 98 | 88 | 12 | 0 |
| (100 g of | 2 | THF | None | 160 | 97 | 88 | 12 | 0 |
| 50% feed) | 3 | THF | None | 360 | 92 | 74 | 26 | 0 |
|  | 4 | THF | EDCl (0.25) | 360 | 94 | 97 | 3 | 0 |
| 5 | 1 | IPOH | EDCL (0.1) | 75 | 98.5 | 94.7 | 5.3 | 0 |
| (100 g of 50% feed) | 2 | IPOH | * | 170 | 96.7 | 77.8 | 20.9 | 1.3 |
| 6 | 1 | IPOH | EDCl (0.5) | 95 | 92.5 | 97.7 | 2.0 | 0.1 |
| (100 g of 50% feed) | 2 | IPOH | * | 835** | 95.3 | 97.1 | 2.9 | 0 |
| 7 | 1 | IPOH | LiCl (0.5) | 340 | 97.8 | 48.6 | 48.5 | 2.59 |
| (100 g of 50% feed) | | | | | | | | |

[a]Catalyst purchased from Engelhard Corporation.
[b]IPOH = isopropanol; THF = tetrahydrofuran
[c]EDCl = dichloroethane; LiCl = lithium chloride; wt. % is based on weight of nitrile feed.
*No additional EDCl added; residual EDCl is present from the first use.
**overnight run; 75% conversion in 350 min.; 90% conversion in 550 minutes.

Examples 1 through 4 show that during the catalytic hydrogenation of butyronitrile there is a decrease in tertiary amine selectivity with catalyst use. However, when dichloroethane is added to the feed at the fourth catalyst use (Examples 1, 3 and 4), the selectivity to tributyl amine substantially increases from as low as 57% to over 90% from the third to fourth use and there is little or no change in hydrogenation time. In addition, the selectivity to tributyl amine was achieved with as little as 0.25 weight % dichloroethane based on the total weight of nitrile (Example 4). In fact, when dichoroethane is added to the catalyst system after three uses, the selectivity to tributyl amine is greater than the selectivity obtained with the first use of the palladium catalyst alone (Examples 1,3 and 4).

When isopropanol is the solvent and no dichloroethane is added (Examples 2 and 3), selectivity to tertiary amine does not exceed 80%. However, when dichloroethane is added, selectivity jumps to over 90% (Example 3, Use 4).

Data from Example 6 show that addition of dichloroethane at the first catalyst use leads to a selectivity of over 95% tributyl amine through two uses of the catalyst. These results are consistent with the results of Example 3 in which selectivity to tributyl amine increased from 57% (third catalyst use) to over 90% (fourth catalyst use), following addition of dichloroethane at the fourth use. The reaction time is longer in Use 2 of Example 6 (95 minutes in Use 1 and 835 minutes in Use 2) because the reaction was allowed to run overnight; however, the selectivity to the tertiary amine is maintained at about 97% through two catalyst uses, as compared to Example 3 in which no dichloroethane is added and the tertiary amine selectivity drops to 73% in two uses. As noted above, in the description of Example 6, Use 2, 75% conversion is obtained in 350 minutes.

Examples 5 and 6 show that the optimum level of dichloroethane is between 0.1 wt. % and 0.5 wt. %, for hydrogenation of butyronitrile. At 0.1 wt. % dichloroethane (Example 5, Use 1), selectivity to tertiary amine decreases to 78% in the second use, indicating that, at the 0.1 wt % level, the effect of dichloroethane is limited to ore use and dichloroethane needs to be added at each use. At 0.5 wt. % dichloroethane (Example 5, Use 1), selectivity to tertiary amine is maintained above 95% through two uses, however catalyst activity decreases. These data show that selectivity to tertiary amines is consistently above 90% when dichloroethane is added to the hydrogenation process; and adjustments in amount of dichloroethane, time of reaction and/or temperature and pressure are needed to obtain an optimum conversion rate while maintaining the selectivity to tertiary amine above about 90% through more than one catalyst use.

Example 7 shows that addition of an inorganic halide, lithium chloride, is ineffective in promoting the production of a tertiary amine. In fact, there is a much longer reaction time for the first use and the selectivity to tributyl amine is much lower when compared to Example 3, in which palladium on alumina alone is used. These results show that an inorganic halide is an unacceptable alternative to an organic halide to enhance selectivity to tertiary amine production.

STATEMENT OF INDUSTRIAL USE

An organic halide is added to the process feed for the catalytic hydrogenation of nitriles in order to obtain high selectivity to tertiary amine production.

What is claimed is:

1. In a process for producing tertiary amines in the catalytic hydrogenation of a saturated or unsaturated aliphatic nitrile comprising contacting the nitrile with hydrogen in the presence of a hydrogenation catalyst, the improvement which comprises:

adding an organic halide having the formula $RX_n$, wherein

R is an aliphatic or aromatic group having 1 to 10 carbon atoms,

X is chloride, bromide or iodide, and n is 1 to the total number of replaceable hydrogens in R.

2. The process of claim 1 wherein the hydrogenation catalyst is selected from the group consisting of platinum, palladium, and rhodium.

3. The process of claim 2 wherein the hydrogenation catalyst is carried on a support.

4. The process of claim 3 wherein the catalyst is palladium and the support is alumina.

5. The process of claim 4 wherein the nitrile is aliphatic and has 2 to 15 carbons.

6. The process of claim 5 wherein the level of organic halide is about 0.01% by weight to about 5% by weight, based on the amount of nitrile.

7. The process of claim 6 wherein R is an aliphatic group.

8. The process of claim 7 wherein R is ethane, X is chloride, and n is 2.

9. The process of claim 8 wherein the nitrile is butyronitrile.

10. The process of claim 9 wherein the level of organic halide is about 0.1% by weight to about 2% by weight based on the weight of nitrile.

11. In a process for producing tertiary amines in the catalytic hydrogenation of a saturated or unsaturated aliphatic nitrile comprising contacting the nitrile with hydrogen in the presence of a hydrogenation catalyst and a solvent, the improvement which comprises:

adding an organic halide having the formula $RX_n$, wherein

R is an aliphatic or aromatic group having 1 to 10 carbon atoms,

X is chloride, bromide or iodide, and n is 1 to the total number of replaceable hydrogens in R.

12. The process of claim 11 wherein the hydrogenation catalyst is selected from the group consisting of platinum, palladium, and rhodium.

13. The process of claim 12 wherein the hydrogenation catalyst is carried on a support.

14. The process of claim 13 wherein the catalyst is palladium and the support is alumina.

15. The process of claim 14 wherein the nitrile is aliphatic and has 2 to 15 carbons.

16. The process of claim 15 wherein the level of organic halide is about 0.01% by weight to about 5% by weight, based on the weight of nitrile.

17. The process of claim 16 wherein R is an aliphatic group.

18. The process of claim 17 wherein R is ethane, X is chloride, and n is 2.

19. The process of claim 18 wherein the solvent is isopropanol and the nitrile is butyronitrile.

20. The process of claim 19 wherein the level of organic halide is about 0.1% by weight to about 2% by weight, based on the weight of nitrile.

* * * * *